(12) United States Patent
Hatanaka et al.

(10) Patent No.: US 12,303,309 B2
(45) Date of Patent: May 20, 2025

(54) MEDICAL IMAGE DISPLAY DEVICE

(71) Applicant: JVCKENWOOD CORPORATION, Yokohama (JP)

(72) Inventors: Masao Hatanaka, Yokohama (JP); Hiroshi Takeshita, Yokohama (JP)

(73) Assignee: JVCKENWOOD CORPORATION, Yokohama (JP)

( * ) Notice: Subject to any disclaimer, the term of this patent is extended or adjusted under 35 U.S.C. 154(b) by 149 days.

(21) Appl. No.: 18/116,474

(22) Filed: Mar. 2, 2023

(65) Prior Publication Data

US 2023/0200766 A1 Jun. 29, 2023

Related U.S. Application Data

(63) Continuation of application No. PCT/JP2021/023748, filed on Jun. 23, 2021.

(30) Foreign Application Priority Data

Sep. 3, 2020 (JP) ................................ 2020-148151

(51) Int. Cl.
*A61B 6/46* (2024.01)
*A61B 6/50* (2024.01)
(Continued)

(52) U.S. Cl.
CPC ........... *A61B 6/462* (2013.01); *G09G 3/3406* (2013.01); *G09G 3/36* (2013.01); *A61B 6/502* (2013.01);
(Continued)

(58) Field of Classification Search
None
See application file for complete search history.

(56) References Cited

U.S. PATENT DOCUMENTS 6,323,869 B1 11/2001 Kohm et al.
10,212,312 B2 * 2/2019 Kimpe .................. G06T 11/001
(Continued)

FOREIGN PATENT DOCUMENTS

CN 107145730 A 9/2017
JP 2004057592 A 2/2004
(Continued)

OTHER PUBLICATIONS

Extended European Search Report issued on May 12, 2023 for application No. EP 21863926.8.
(Continued)

*Primary Examiner* — Ryan M Gray
(74) *Attorney, Agent, or Firm* — Nath, Goldberg & Meyer; Jerald L. Meyer

(57) ABSTRACT

An adjustment value holding unit holds an adjustment value selected for displaying medical image data on a medical image display device with a predetermined image quality. An image attribute detector detects an attribute of the medical image data. A determiner determines whether or not the adjustment value held in the adjustment value holding unit matches an adjustment value corresponding to the attribute detected by the image attribute detector. A notification unit visually or audibly notifies that the adjustment value held in the adjustment value holding unit does not match the adjustment value suitable for the medical image to be displayed on the medical image display device, when the determiner determines that the adjustment value held in the adjustment value holding unit does not match the adjustment value corresponding to the attribute detected by the image attribute detector.

3 Claims, 5 Drawing Sheets

(51) Int. Cl.
*G09G 3/34* (2006.01)
*G09G 3/36* (2006.01)

(52) U.S. Cl.
CPC ............. *G09G 2320/0276* (2013.01); *G09G 2320/062* (2013.01); *G09G 2320/0626* (2013.01); *G09G 2320/08* (2013.01); *G09G 2380/08* (2013.01)

(56) References Cited

U.S. PATENT DOCUMENTS

| | | | | |
|---|---|---|---|---|
| 2012/0229490 | A1* | 9/2012 | Rezaee | G09G 5/10 345/589 |
| 2015/0278442 | A1* | 10/2015 | Rezaee | G16H 30/40 382/128 |
| 2016/0027168 | A1* | 1/2016 | Ikeda | G09G 3/3426 345/593 |
| 2016/0054969 | A1* | 2/2016 | Maruyama | G06F 3/1446 345/690 |
| 2017/0213524 | A1* | 7/2017 | Tsunamoto | G09G 5/00 |

FOREIGN PATENT DOCUMENTS

| | | |
|---|---|---|
| JP | 2004159986 A | 6/2004 |
| JP | 2015019815 A | 2/2015 |
| JP | 2015066014 A | 4/2015 |

OTHER PUBLICATIONS

Office Action issued on Feb. 20, 2024 in the counterpart Japanese application No. 2020-148151.

* cited by examiner

| | GRADATION CHARACTERISTIC | MAXIMUM LUMINANCE |
|---|---|---|
| ADJUSTMENT VALUE 1 (FOR MAMMOGRAPHY IMAGES) | DICOM GSDF | 500cd/m² |
| ADJUSTMENT VALUE 2 (FOR CHEST X-RAY IMAGES) | DICOM GSDF | 350cd/m² |
| ADJUSTMENT VALUE 3 (FOR COLOR IMAGES) | GAMMA 2.2 | 350cd/m² |

FIG. 6

| | | BRIGHTNESS | GRADATION CHARACTERISTIC | MAXIMUM LUMINANCE |
|---|---|---|---|---|
| ADJUSTMENT VALUE 1 (FOR MAMMOGRAPHY IMAGES) | ADJUSTMENT VALUE 1A | BRIGHT | DICOM GSDF | 550cd/m² |
| | ADJUSTMENT VALUE 1B | DARK | DICOM GSDF | 500cd/m² |
| ADJUSTMENT VALUE 2 (FOR CHEST X-RAY IMAGES) | ADJUSTMENT VALUE 2A | BRIGHT | DICOM GSDF | 380cd/m² |
| | ADJUSTMENT VALUE 2B | DARK | DICOM GSDF | 350cd/m² |
| ADJUSTMENT VALUE 3 (FOR COLOR IMAGES) | ADJUSTMENT VALUE 3A | BRIGHT | GAMMA 2.2 | 550cd/m² |
| | ADJUSTMENT VALUE 3B | DARK | GAMMA 2.2 | 500cd/m² |

MEDICAL IMAGE DISPLAY DEVICE

CROSS REFERENCE TO RELATED APPLICATION

This application is a Continuation of PCT Application No. PCT/JP2021/023748 filed on Jun. 23, 2021, and claims the priority of Japanese Patent Application No. 2020-148151 filed on Sep. 3, 2020, the entire contents of both of which are incorporated herein by reference.

BACKGROUND

The present disclosure relates to a medical image display device.

In the medical field, a medical image based on medical image data such as chest X-ray (radiograph) image data or mammography image data is displayed on a medical image display device, and a doctor may diagnose a patient by viewing the medical image. Generally, various types of medical images are stored in a picture archiving and communication system (PACS) server. A workstation reads a medical image from the PACS server, and the medical image display device displays the medical image on a display.

Medical image display devices are not necessarily classified into image display devices dedicated to displaying mammography images and image display devices dedicated to displaying chest X-ray images. Thus, a single medical image display device may display a mammography image or a chest X-ray image on a display.

SUMMARY

The adjustment values of a medical image display device for displaying mammography images with suitable image quality are different from those of a medical image display device for displaying chest X-ray images with suitable image quality. For example, if a chest X-ray image is displayed while a medical image display device is set to display mammography images with suitable image quality, the doctor may not be able to make an accurate diagnosis.

Mammography and chest X-ray images are monochrome images, while endoscopic and ultrasound diagnostic images are color images. A medical image display device includes a display (color panel) that can display color images, and the adjustment value that provides suitable image quality for displaying monochrome images on the color panel and the adjustment value that provides suitable image quality for displaying color images on the color panel are different. For example, if a monochrome image is displayed on the medical image display device while the medical image display device is set to display color images with suitable image quality for displaying color images, the doctor may not be able to make an accurate diagnosis.

In this way, if the adjustment value set in the medical image display device is not suitable for the medical image to be displayed, the displayed image quality may not be optimal and the doctor may not be able to make an accurate diagnosis. Therefore, it is desirable to develop a medical image display device that can avoid a mismatch between the adjustment value set in the medical image display device and the adjustment value suitable for the medical image to be displayed.

An aspect of one or more embodiments provides a medical image display device including: an adjustment value holding unit configured to hold an adjustment value selected for displaying medical image data on a medical image display device with a predetermined image quality; an image attribute detector configured to detect an attribute of the medical image data; a determiner configured to determine whether or not the adjustment value held in the adjustment value holding unit matches an adjustment value corresponding to the attribute detected by the image attribute detector; and a notification unit configured to visually or audibly notify that the adjustment value held in the adjustment value holding unit does not match an adjustment value suitable for the medical image to be displayed on the medical image display device, when the determiner determines that the adjustment value held in the adjustment value holding unit does not match the adjustment value corresponding to the attribute detected by the image attribute detector.

BRIEF DESCRIPTION OF THE DRAWINGS

FIG. 6 is a table illustrating an example of adjustment values for image quality stored in an adjustment value storage unit of FIG. 5.

DETAILED DESCRIPTION

Hereinafter, the medical image display device according to each embodiment will be described with reference to the accompanying drawings.

First Embodiment

Figure 1:
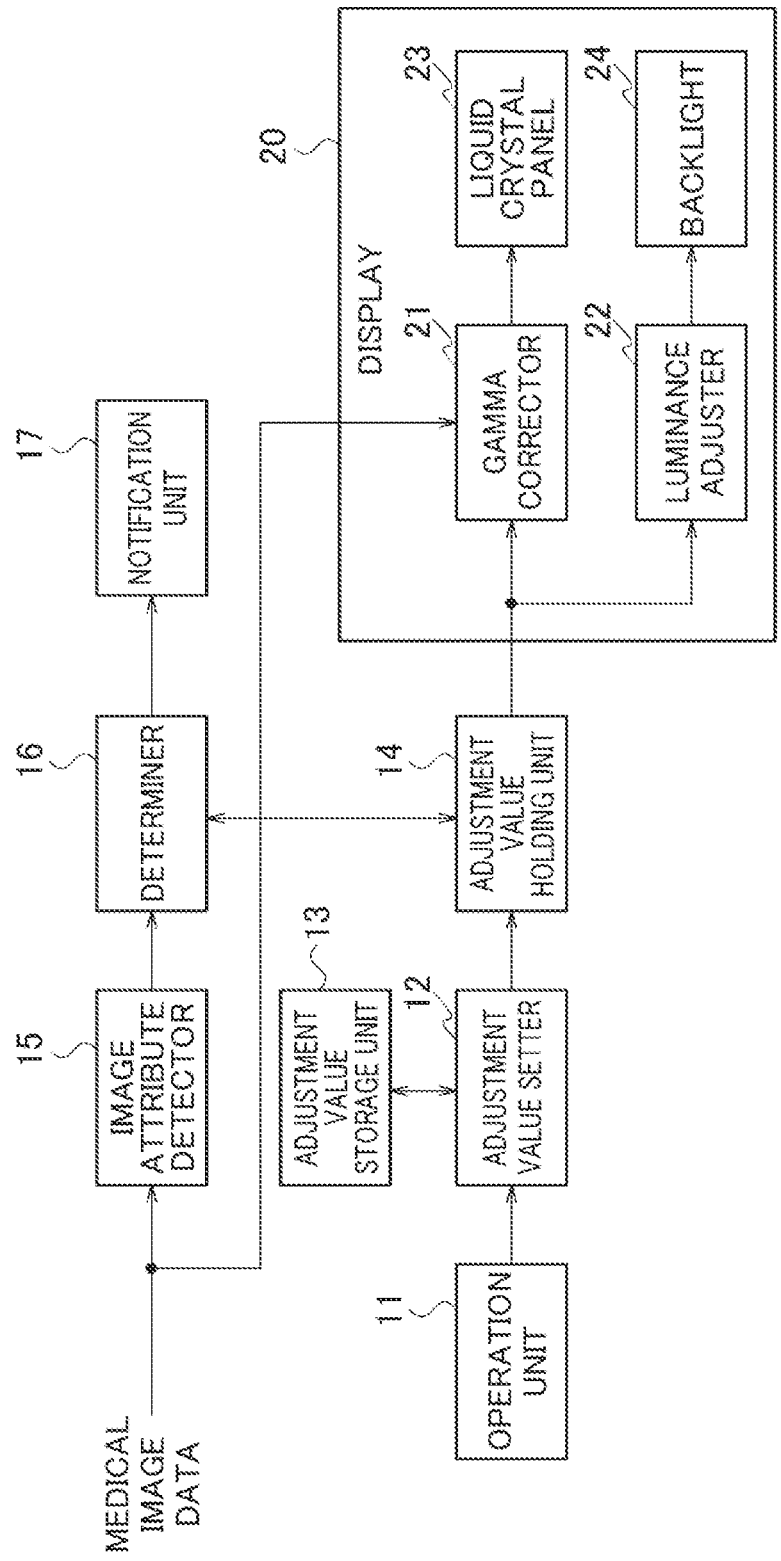
FIG. 1 is a block diagram illustrating a medical image display device according to a first embodiment.

In FIG. 1, medical image data read from a PACS server by an unillustrated workstation is supplied to an image attribute detector 15 and a display 20.

Figures 2, 3:
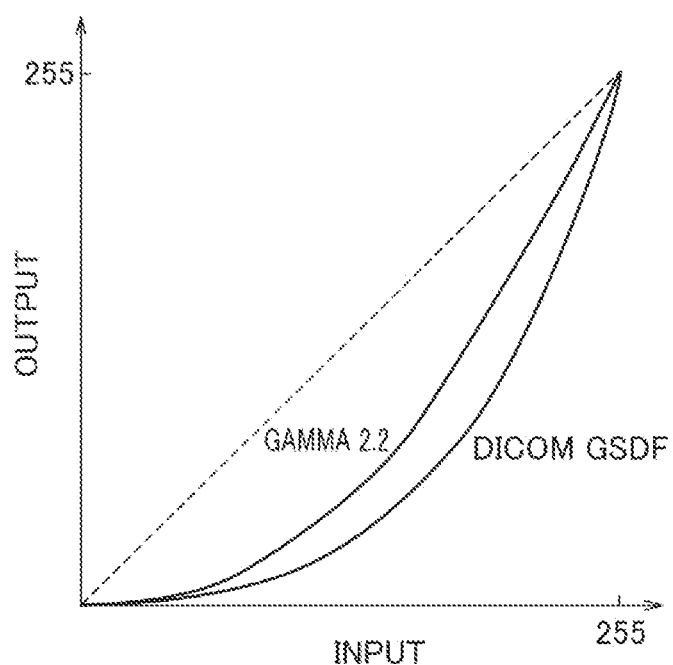
FIG. 2 is a table illustrating an example of adjustment values for image quality stored in an adjustment value storage unit of FIG. 1.
FIG. 3 is a characteristic diagram illustrating gradation characteristics of DICOM GSDF and gamma 2.2.

An adjustment value storage unit 13 stores adjustment values for adjusting image quality when various types of medical images are to be displayed on the display 20. The adjustment value storage unit 13 is a ROM, for example. As shown in FIG. 2, an adjustment value is a combination of a gradation characteristic and a maximum luminance, and the adjustment value storage unit 13 stores three adjustment values, adjustment values 1 to 3, for example. The adjustment value 1 is an adjustment value for mammography images, the adjustment value 2 is an adjustment value for chest X-ray images, and the adjustment value 3 is an adjustment value for color images. When a liquid crystal panel 23 is a monochrome panel, the adjustment value 3 is not required.

DICOM GSDF shown in FIG. 2 is gradation characteristic using a grayscale standard display function (GSDF) conforming to the digital imaging and communications in medicine (DICOM) standard. Gamma 2.2 shown in FIG. 2 is a gradation characteristic having a gamma value of 2.2. Assuming that the medical image data is 8 bits, DICOM GSDF and gamma 2.2 have gradation characteristics indicating the input/output characteristics shown in FIG. 3.

Returning to FIG. 1, an operator such as a doctor or nurse operates an operation unit 11 to select an adjustment value according to the medical image to be displayed on the display 20. A plurality of adjustment values may be toggled by operating the operation unit 11, or a menu for selecting an adjustment value may be displayed on the display 20 by operating the operation unit 11, and one of the adjustment values may be selected. When an operation to select an adjustment value is performed by the operation unit 11, an adjustment value setter 12 reads the selected adjustment value from the adjustment value storage unit 13 and causes an adjustment value holding unit 14 to hold the selected adjustment value. The adjustment value holding unit 14 is a non-volatile memory, for example.

The display 20 includes a gamma corrector 21, a luminance adjuster 22, the liquid crystal panel 23, and a backlight 24. The gamma corrector 21 performs a gamma correction on the input medical image data with the gradation characteristic shown in FIG. 3. The luminance adjuster 22 controls the luminance of the backlight 24 to adjust the maximum luminance of the medical image displayed on the liquid crystal panel 23. The maximum luminance of the medical image displayed on the liquid crystal panel 23 is determined by the luminance of the backlight 24.

For example, if the operator selects the adjustment value 1 and the adjustment value holding unit 14 holds the adjustment value 1, the gamma corrector 21 performs a gamma correction on the input medical image data so as to have the gradation characteristic of DICOM GSDF. The luminance adjuster 22 controls the luminance of the backlight 24 so that the maximum luminance is 500 $cd/m^2$.

The image attribute detector 15 detects an attribute indicating the type of medical image by analyzing a tag (DICOM tag) attached to the medical image data. The image attribute detector 15 analyzes the tag to detect whether the medical image data is a mammography image or a chest X-ray image.

To explain the DICOM tag specifically, the DICOM tag includes "(0008, 0060)", which stores the type of device (modality) that generated the image, what is called the modality code. The modality code is represented by two letters of the alphabet, and MG indicates mammography, for example. If the modality code described in (0008, 0060) of the DICOM tag is MG, it can be detected that the device that generated the medical image data is a mammography device and the medical image data is a mammography image.

The image attribute 15 may detect the attribute of the medical image data by combining the DICOM tag (0008, 0060) and other tag information.

A determiner 16 determines whether or not the adjustment value held in the adjustment value holding unit 14 is an adjustment value corresponding to the attribute detected by the image attribute detector 15. The determiner 16 supplies the determination result to a notification unit 17. The fact that the adjustment value held in the adjustment value holding unit 14 does not correspond to the attribute detected by the image attribute detector 15 means that the image quality set in the medical image display device does not match the image quality suitable for the medical image to be displayed on the display 20.

Therefore, when the determination result by the determiner 16 indicates a mismatch, the notification unit 17 visually or audibly informs the user of the medical image display device that the adjustment value held in the adjustment value holding unit 14 is not suitable for the medical image to be displayed on the display 20. The notification unit 17 may be a warning light such as an LED, or may be a speaker. When the medical image data is image data of a chest X-ray image and the adjustment value 1 is selected, the notification unit 17 may output a notification such as "please adjust the maximum luminance to 350 $cd/m^2$" or "please select the adjustment value 2".

The user who has received the notification from the notification unit 17 can operate the operation unit 11 to select an appropriate adjustment value according to the medical image to be displayed on the display 20. Thus, according to a first embodiment, it is possible to avoid a mismatch between the image quality set in the medical image display device and the image quality suitable for the medical image to be displayed on the medical image display device.

Figure 4:
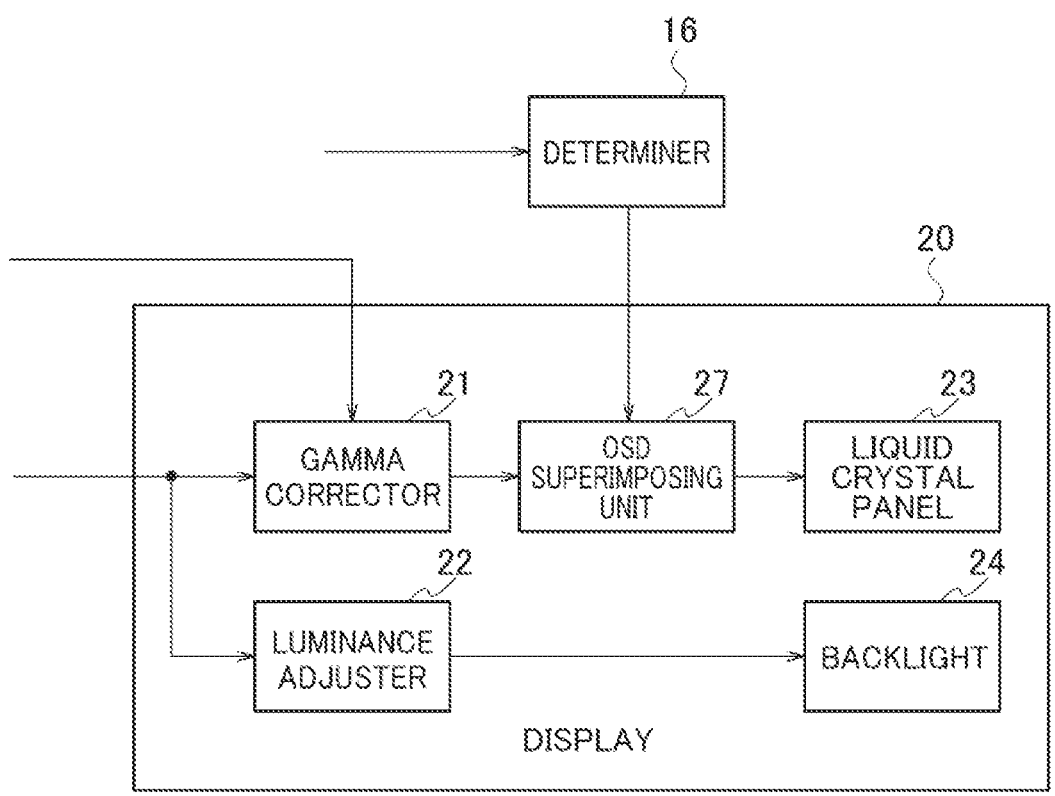
FIG. 4 is a block diagram illustrating a modified example of the medical image display device according to a first embodiment.

As shown in FIG. 4, an on-screen display (OSD) superimposing unit 27 included in the display 20 may function as the notification unit 17. When the determination result by the determiner 16 indicates a mismatch, the OSD superimposing unit 27 superimposes text information or image information indicating that the adjustment value is inappropriate, on the gamma-corrected medical image data output from the gamma corrector 21, and supplies it to the liquid crystal panel 23.

The user can recognize that the adjustment value is not appropriate due to the text information or image information superimposed on the medical image displayed on the liquid crystal panel 23, and can select an appropriate adjustment value.

Second Embodiment

Figure 5:
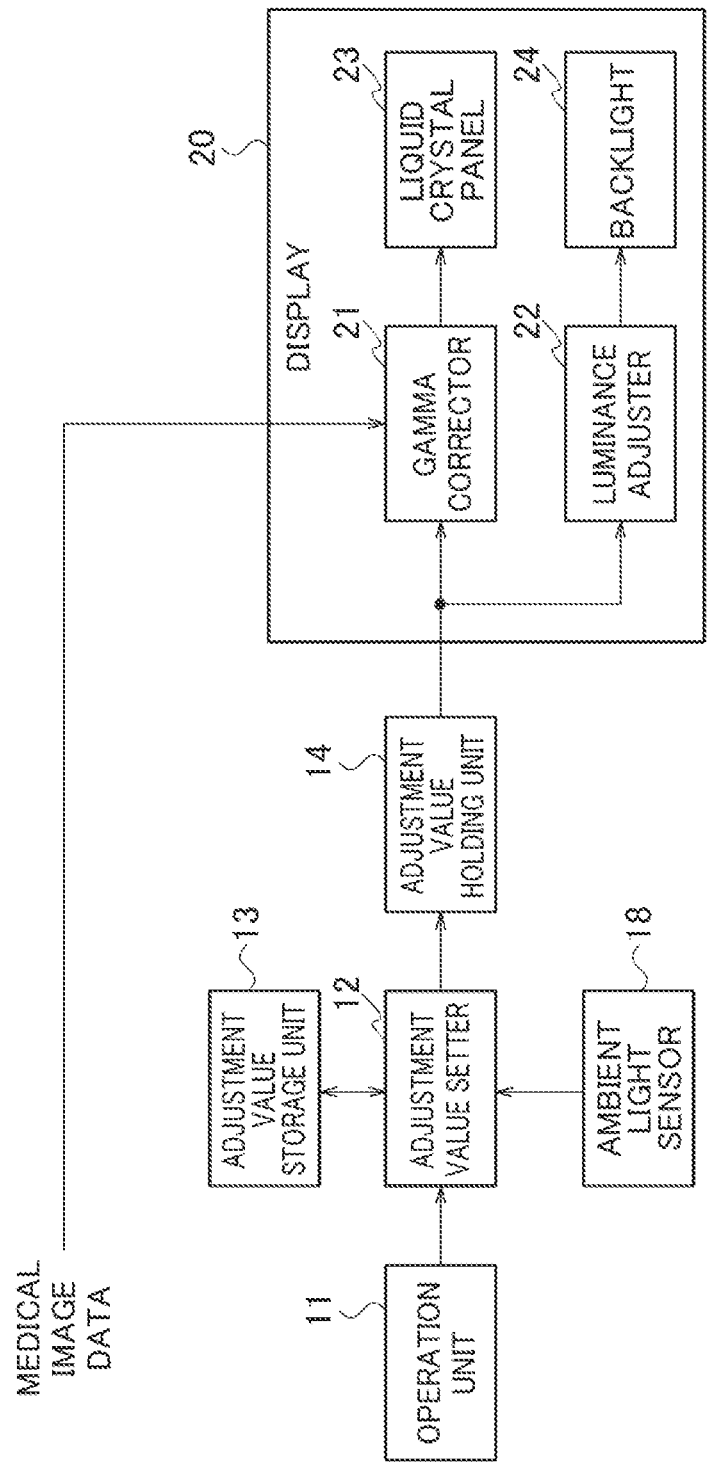
FIG. 5 is a block diagram illustrating a medical image display device according to a second embodiment.

The purpose of a second embodiment shown in FIG. 5 is to adjust the image quality to be more appropriate according to the brightness of the ambient light surrounding the medical image display device. In FIG. 5, the same parts as those in FIG. 1 are denoted by the same reference numerals, and the description thereof may be omitted.

As shown in FIG. 6, the adjustment value storage unit 13 stores three adjustment values 1 to 3 as adjustment values that can be recognized by operators such as doctors and nurses, for example. In a second embodiment, each of the adjustment values 1 to 3 consists of two adjustment values, one suitable for bright surroundings and one suitable for dark surroundings.

The adjustment value 1 for mammography images includes an adjustment value 1A suitable for bright surroundings and an adjustment value 1B suitable for dark surroundings. The adjustment value 2 for chest X-ray images includes an adjustment value 2A suitable for bright surroundings and an adjustment value 2B suitable for dark surroundings. The adjustment value 3 for color images includes an adjustment value 3A suitable for bright surroundings and an adjustment value 3B suitable for dark surroundings.

Bright surroundings are defined as the surrounding brightness being equal to or higher than a predetermined brightness, and dark surroundings are defined as the surrounding brightness being less than the predetermined brightness. In the example shown in FIG. 6, the maximum luminance is made to be different between when the surroundings are bright and when the surroundings are dark. The brightness of the surroundings may be divided into three or more levels, and the maximum luminance may be varied in three or more levels. Although one of the adjustment values 1 to 3 can bb selected as the adjustment value, the adjustment values 1A, 1B, 2A, 2B, 3A, and 3B cannot be directly selected.

In FIG. 5, an ambient light sensor 18 detects whether the ambient brightness is equal to or greater than a predetermined brightness, or less than the predetermined brightness. The operator operates the operation unit 11 to select one of the adjustment values 1 to 3 according to the medical image to be displayed on the display 20. The adjustment value setter 12 selects an adjustment value corresponding to the selection value selected by the operator and according to the brightness detected by the ambient light sensor 18. The adjustment value setter 12 reads the selected adjustment value from the adjustment value storage unit 13 and causes the adjustment value holding unit 14 to hold the selected adjustment value.

The adjustment value holding unit 14 holds the adjustment value 1A or 1B when the operator selects the adjustment value 1, the adjustment value 2A or 2B when the operator selects the adjustment value 2, and the adjustment value 3A or 3B when the operator selects the adjustment value 3.

According to a second embodiment, it is possible to adjust the image quality to be more appropriate according to the brightness of the ambient light surrounding the medical image display device. A medical image display device may be configured by combining a first embodiment and a second embodiment.

The present invention is not limited to first and second embodiments described above, and various modifications can be made without departing from the scope of the present invention. The display 20 is not limited to a configuration including the liquid crystal panel 23, and may be configured to include an organic EL panel. In this case, the backlight 24 is not necessary, and the luminance adjuster 22 adjusts the maximum luminance when the organic EL panel emits light.

In FIG. 1 or 5, the adjustment value setter 12, the image attribute detector 15, and the determiner 16 may be configured by means of a microcomputer or microprocessor. A part of the medical image display device may be configured by means of software (computer program). The use of hardware or software is optional. Furthermore, some of the functions of the medical image display device may be realized by a means of a computer device connected to the medical image display device.

What is claimed is:

1. A medical image display device comprising:
 an adjustment value holding unit configured to hold an adjustment value selected for displaying medical image data on a medical image display device with a predetermined image quality;
 an image attribute detector configured to detect an attribute of the medical image data;
 a determiner configured to determine whether or not the adjustment value held in the adjustment value holding unit matches an adjustment value corresponding to the attribute detected by the image attribute detector; and
 a notification unit configured to visually or audibly notify a user of the medical image display device that the adjustment value held in the adjustment value holding unit does not match an adjustment value suitable for the medical image to be displayed on the medical image display device, to visually or audibly instruct the user to adjust an adjustment value of the medical image display device to an adjustment value corresponding to the attribute of the medical image data, and to visually or audibly notify the user the adjustment value of the medical image display device corresponding to the attribute of the medical image data, when the determiner determines that the adjustment value held in the adjustment value holding unit does not match the adjustment value corresponding to the attribute detected by the image attribute detector.

2. The medical image display device according to claim 1, further comprising an adjustment value storage unit storing adjustment values corresponding to each medical image data in a plurality of medical image data having different attributes from each other,
 wherein the adjustment value storage unit stores a plurality of adjustment values corresponding to ambient brightness of the medical image display device as the adjustment values corresponding to the each medical image data.

3. The medical image display device according to claim 2, further comprising:
 an ambient light sensor configured to detect the ambient brightness;
 an operation unit configured to select an adjustment value for the medical image data to be displayed on the medical image display device from the adjustment values corresponding to the each medical image data stored in the adjustment value storage unit; and
 an adjustment value setter configured to select an adjustment value according to the ambient brightness detected by the ambient light sensor corresponding to the selected adjustment value selected by the operator using the operation unit from the adjustment values corresponding to the ambient brightness of the medical image display device, and to cause the adjustment value holding unit to hold the selected adjustment value.

\* \* \* \* \*